(12) United States Patent
Delage-Grouiller et al.

(10) Patent No.: US 8,986,667 B2
(45) Date of Patent: *Mar. 24, 2015

(54) COSMETIC COMPOSITION WITH SKIN TIGHTENING EFFECT

(75) Inventors: Hervé Delage-Grouiller, Le Kremlin Bicetre (FR); Brigitte Noe, Orleans (FR); Christian Mahe, Rennes (FR)

(73) Assignee: LVMH Recherche, Paris (FR)

( * ) Notice: Subject to any disclaimer, the term of this patent is extended or adjusted under 35 U.S.C. 154(b) by 651 days.

This patent is subject to a terminal disclaimer.

(21) Appl. No.: 12/585,755

(22) Filed: Sep. 24, 2009

(65) Prior Publication Data

US 2010/0021404 A1    Jan. 28, 2010

Related U.S. Application Data

(63) Continuation of application No. 10/487,693, filed as application No. PCT/FR02/02941 on Aug. 27, 2002, now Pat. No. 7,700,084.

(30) Foreign Application Priority Data

Aug. 27, 2001  (FR) ...................................... 01 11123

(51) Int. Cl.
| | | |
|---|---|---|
| *A61K 31/047* | (2006.01) | |
| *A61K 31/734* | (2006.01) | |
| *A61K 31/715* | (2006.01) | |
| *A61Q 19/00* | (2006.01) | |
| *A61K 8/02* | (2006.01) | |
| *A61K 8/34* | (2006.01) | |
| *A61K 8/73* | (2006.01) | |
| *A61K 8/81* | (2006.01) | |
| *A61Q 19/08* | (2006.01) | |

(52) U.S. Cl.
CPC .............. *A61Q 19/00* (2013.01); *A61K 31/715* (2013.01); *A61K 31/047* (2013.01); *A61K 8/0212* (2013.01); *A61K 8/345* (2013.01); *A61K 8/731* (2013.01); *A61K 8/733* (2013.01); *A61K 8/8129* (2013.01); *A61K 8/8176* (2013.01); *A61K 2800/5422* (2013.01); *A61K 2800/5424* (2013.01); *A61K 2800/594* (2013.01); *A61Q 19/08* (2013.01)
USPC .................. 424/78.03; 424/195.17; 424/765; 514/738; 514/54; 514/57; 536/1.11; 536/2; 536/3; 536/123.13

(58) Field of Classification Search
CPC . A61K 31/734; A61K 31/732; A61K 31/731; A61K 31/715; A61K 31/047; A61K 31/765; A61K 31/79; A61K 31/717
USPC ...................................................... 514/183
See application file for complete search history.

(56) References Cited

U.S. PATENT DOCUMENTS

| | | | |
|---|---|---|---|
| 4,126,142 A | 11/1978 | Saute | |
| 5,416,205 A | 5/1995 | della Valle et al. | |
| 5,578,307 A * | 11/1996 | Wunderlich et al. | .......... 424/744 |
| 6,030,643 A * | 2/2000 | Adams et al. | .................. 424/464 |
| 6,193,975 B1 * | 2/2001 | Bonte et al. | .................... 424/725 |
| 6,269,817 B1 | 8/2001 | Nagashima et al. | |
| 7,105,184 B2 | 9/2006 | Pauly et al. | |

FOREIGN PATENT DOCUMENTS

| | | |
|---|---|---|
| EP | 0 614 914 A2 | 9/1994 |
| EP | 1 151 751 A1 | 11/2001 |
| JP | 52-79034 | 7/1977 |
| JP | 52079034 | 7/1977 |
| JP | 63313709 | 12/1988 |
| JP | 02-053707 | 2/1990 |
| JP | 02053707 | 2/1990 |
| JP | 05-000933 | 1/1993 |
| JP | 05032523 | 2/1993 |
| JP | 6065048 | 3/1994 |
| JP | 10-182408 | 7/1998 |
| JP | 10-279466 | 10/1998 |
| KR | 2001089938 | 10/2001 |
| RU | 2069557 | 11/1996 |

OTHER PUBLICATIONS

Makinen et al., A quantitative study of mannitol, sorbitol, xylitol, and xylose in wild berries and commerical fruits, 1980 Journal of Food science, vol. 45, Issue 2, pp. 367-371, Abstract Only.*
XP-0022051155, p. 45, #240,241, Algin, Alginic acid, 1996 Abstract Only.
XP-002205156, p. 1490, # 8873,, Sorbitol, 1996 Abstract Only.

* cited by examiner

*Primary Examiner* — James D Anderson
*Assistant Examiner* — Meghan Finn
(74) *Attorney, Agent, or Firm* — Nath, Goldberg & Meyer; Tanya E. Harkins; Joshua B. Goldberg

(57) ABSTRACT

The present invention relates to a mixture, having a skin-tightening effect, which is made up of:
- 10 to 80% by weight of a polysaccharide, preferably of an alginate, having a molecular weight of less than 600,000 Daltons, preferably less than 400,000 Daltons and more preferably less than 200,000 Daltons,
- 15 to 75% by weight of a polyhydroxylated agent selected from sugars and their derivatives, particularly sugar esters and sugar, ethers, preferably sorbitol,
- 3 to 15% by weight of poly(vinyl alcohol) or polyvinylpyrrolidone, and
- 0 to 25% by weight of cellulose or of a derivative of cellulose, such as carboxymethylcellulose or hydroxymethylcellulose.

Figure 1:
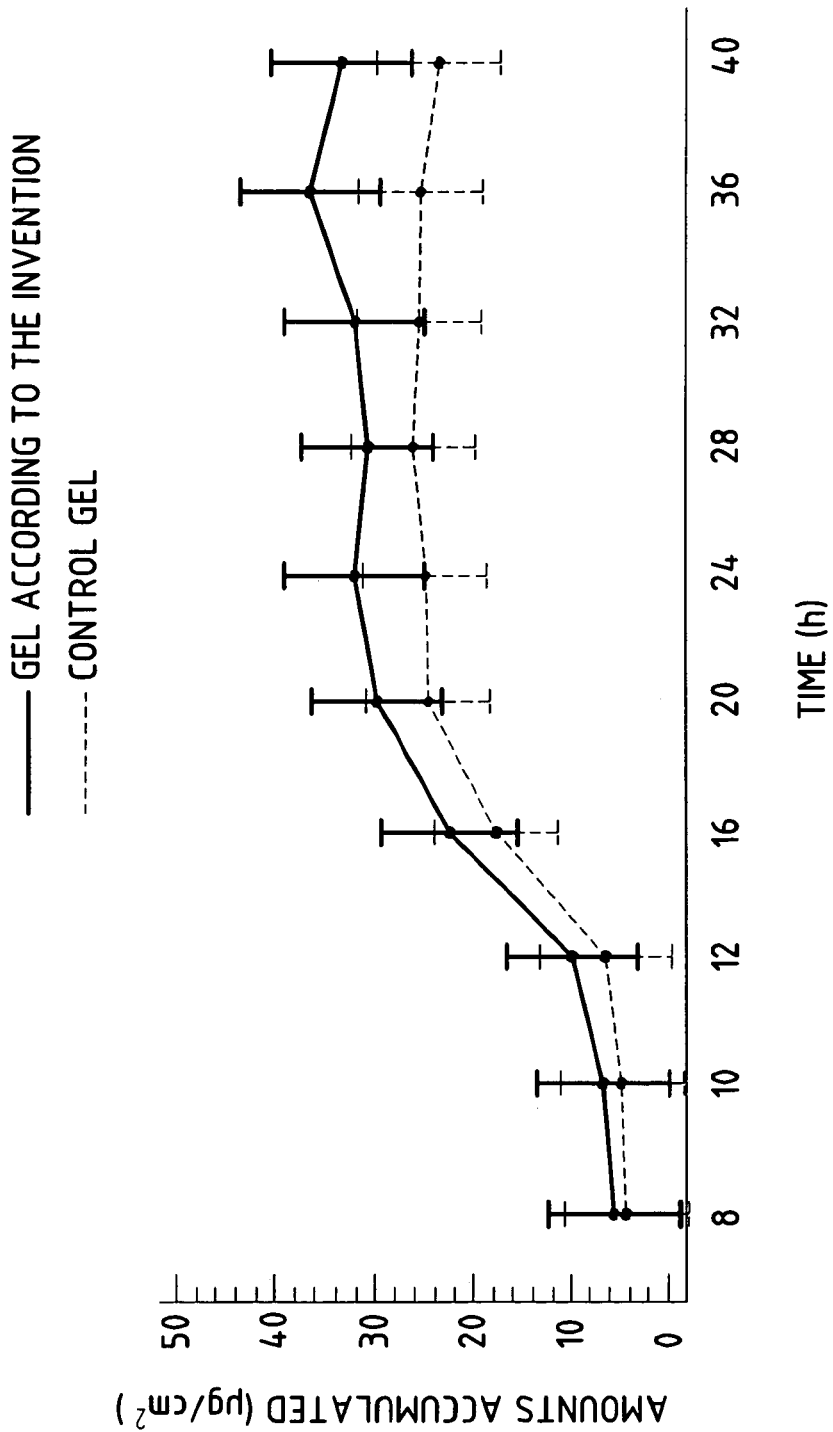

The present invention also relates to cosmetic compositions which contain this mixture.
These cosmetic compositions enable a mechanical smoothing of the surface of the skin to be obtained progressively with great comfort of use and enables a good fixing of make-up products.

34 Claims, 2 Drawing Sheets

COSMETIC COMPOSITION WITH SKIN TIGHTENING EFFECT

This is a Continuation Application of U.S. patent application Ser. No. 10/487,693, filed Feb. 26, 2004, which was filed under 35 U.S.C. 371 as a national stage of PCT/FR02/02941, filed Aug. 27, 2002, and claims benefit to French Priority Application No. 0111123, filed on Aug. 27, 2001, the entire content of each of which is hereby incorporated by reference in its entirety.

The invention relates essentially to a mixture having a tightening effect on the surface of the skin, as well as to its use for preparing a cosmetic composition having a tightening effect for smoothing the surface of the skin.

It is known from the document FR-A-2,478,468 of a composition which comprises a mixture of two fractions of hyaluronate of different molecular weight, one having a low molecular weight of the order of 10,000 to 200,000 Daltons and the other of high molecular weight of the order of 1,000,000 to 4,500,000 Daltons, in a determined weight ratio of between 0.3 and 2, a protein originating from the natural substance being used as source of hyaluronate, as well as water as the remainder.

This composition can also contain 0.05 to 5% of sugar-alcohol such as sorbitol, as well as 0.2% to 1% of polysaccharide such as an alginate. This document does not disclose in any way the use of products having a tightening effect in the sense of the present invention. It emerges from the description of this patent application that the composition is described essentially as having a moisturising effect.

It is also known from the document WO 96/19180 of the use, in a composition notably for toning up the skin, of polysaccharides combined with caseine. Said polysaccharides are used at low concentration as a filmogenic agent. This document does not disclose in any way that the composition described possesses any effect of mechanical smoothing of the surface of the skin.

Japanese patent application JP 60 55048 describes cosmetic compositions which contain, as essential constituents, 25 to 80% by weight of sodium alginate and 15 to 70% of polyhydric alcohol. These compositions possess a good quality of adhesion to the skin and of moisturisation of it.

It has now been established, during tests carried out by the inventors of the present invention with the view to developing a product having a tightening effect on the surface of the skin, that surprisingly, the introduction of poly(vinyl alcohol) or polyvinylpyrrolidone in mixtures containing a polysaccharide and a sugar or a sugar derivative enabled the properties of adhesion to the skin to be greatly improved and that besides, the addition of cellulose or of a derivative of cellulose to this mixture comprising the three constituents (polysaccharide, sugar or sugar derivative and poly(vinyl alcohol) and/or polyvinylpyrrolidone), enabled any sensation of pulling of the skin to be avoided, in conferring elasticity to the polymeric matrix which is formed after application of the composition on the skin, without causing loosening for all that.

This led the inventors of the present invention to define novel mixtures of products which possess remarkable cosmetic properties and which enable properties of a tightening effect on the skin, and of adhesion to the skin, to be conferred to cosmetic compositions in which they are incorporated, which properties have not been hitherto observed and which are linked to the simultaneous presence in the mixture of a polysaccharide, of a sugar or a sugar derivative and of poly(vinyl alcohol) or polyvinylpyrrolidone and, eventually, of cellulose or of cellulose derivatives, in well-defined proportions.

It emerges from the documentary study made by the inventors of the present invention that even if various documents of the literature envisage the presence of some of these constituents, even their whole in combination, none reveals or suggests the particular proportions of these constituents for obtaining a remarkable tightening effect obtained according to the present invention.

Thus, Japanese patent JP-2053707 describes cosmetic compositions which form a very thin film on the skin intended to reduce wrinkles and to nourish the skin. The compositions described in this document essentially contain 0.2% of poly(vinyl alcohol), 2% of hydroxymethylcellulose, 0.5% of sodium alginate, 5% of modified alcohol, 4.96% of moisturising agent and 87.34% of water. This document does not therefore suggest the introduction of a sugar.

Russian patent RU-2069557 describes a moisturising and cleansing cream which contains, amongst other constituents, methylcellulose, or sodium alginate and glycerine.

This composition does not possess any tightening effect of the skin, nor any effect of mechanical smoothing of wrinkles.

The patent JP-5207934 describes a cosmetic composition having a reduced content of poly(vinyl alcohol) nourishing the skin. This composition contains alginate as thickening agent at contents which do not enable the tightening effect sought after according to the present invention, to be obtained.

Japanese application JP-5032523 describes cosmetic compositions which contain a hydrosoluble polymer which can contain, inter alia, cellulose, or sodium alginate, as well as optionally poly(vinyl alcohol). This product is described as having an oil-absorbent effect and as providing a sensation of freshness, and has no tightening effect on the skin.

The Korean application, published under the number KR-2001089938 was published on Oct. 17, 2001 and describes cosmetic compositions intended to moisturise and to whiten the skin. These compositions contain 3.4% of poly(vinyl alcohol), 16.6% of sorbitol, 4.7% of glycerine, 30.2% of zeolite, 3.6% of talc, 0.14% of chitosan, 0.26% of sodium alginate and 41.1% of natural plant extracts in alcohol. The very low concentrations of polysaccharide of the compositions described in this document do not enable in any way the tightening effect sought after according to the present invention; to be obtained.

The present invention enables a novel mixture, having a tightening effect on the surface of the skin, to be obtained for the preparation of a cosmetic composition having a tightening effect in a controlled manner, and enabling a visible and lasting smoothing of the surface of the skin with a great comfort of use.

The present invention also relates to solving the novel technical problem consisting of providing a novel product, notably having a tightening effect on the surface of the skin, capable of acting effectively in order to give a smoothing of the surface of the skin in notably obtaining a total or partial erasure of wrinkles, including medium and deep wrinkles.

The present invention enables this novel technical problem to be solved for the first time in a satisfactory, safe and reliable manner, which can be used on an industrial and cosmetic scale.

Thus, the invention relates, according to one of its essential features, to a mixture, having a skin-tightening effect, which is made up of:

10 to 80% by weight of a polysaccharide having a molecular weight of less than 600,000 Daltons, preferably less than 400,000 Daltons and more preferably less than 200,000 Daltons, 15 to 75% by weight of a polyhydroxylated agent selected from sugars and their derivatives, particularly sugar esters and sugar ethers, 3 to 15% by weight of poly(vinyl alcohol) or polyvinylpyrrolidone, and 0 to 25% by weight of cellulose or of a derivative of cellulose, such as carboxymethylcellulose or hydroxymethylcellulose.

Advantageously, the above-mentioned polysaccharide is a pectin, a carrageenan, a galactomanane, a xanthan or an alginate.

According to a preferred embodiment, the polysaccharide is an alginate, particularly an alginate of propylene glycol, or an alginate in the form of an acid or a salt, particularly a sodium alginate.

Amongst the commercial alginates which can be used in the compositions according to the present invention, those of Manugel type can be cited.

According to another particularly advantageous embodiment of the invention, the above-mentioned polysaccharide is an alginate which is in the form of an extract of alga, particularly an extract of alga of the family of Laminariacae, preferably an extract of *Laminaria digitata* alga, of *Laminaria flexicaulis* alga, or even of *Laminaria saccharina* alga. Commercial extracts of algae do exist which are suitable for the implementation of the invention. They are notably commercialised by the company 1 dB Holding, such as, for example: *Laminaria digitata* extract, *Laminaria saccharina* extract, Laminarine, or even Phytelene of *Laminaria* EG 483 liquid and EG 749.

According to an advantageous variant of the invention, the concentration of polysaccharide is between 20 and 55% by weight with respect to the total weight of said mixture.

Advantageously, the polyhydroxylated agent is selected from sugars and their derivatives, particularly their esters or their ethers.

Preferably, the sugar is selected from $C_6$ sugars and $C_{12}$ sugars.

Advantageously, the $C_6$ sugar is selected from glucose, sorbitol, mannitol and galactitol, the $C_{12}$ sugar is selected from sucrose and lactitol.

According to an advantageous embodiment, the polyhydroxylated agent is sorbitol.

According to a variant of the invention, the polyhydroxylated agent is sorbitol and is in the form of a plant extract, particularly an extract of sorbs, such as a *Sorbus aucuparia* sorb extract, a *Sorbus domestica* sorb extract, or a *Sorbus aria* sorb extract.

According to another advantageous variant of the invention, the concentration of polyhydroxylated agent is 40 and 65% by weight with respect to the total weight of said mixture.

According to a particularly preferred embodiment of the invention, the mixture, having a tightening effect on the surface of the skin, contains a *Laminaria flexicaulis* extract and an extract of sorbs, particularly an extract of *Sorbus aucuparia*.

According to a particularly advantageous embodiment of the invention, the concentration of polysaccharide is greater than the concentration of polyhydroxylated agent.

According to this embodiment, it was observed that the higher polysaccharide concentration enables a matt appearance to be obtained after application of a composition containing said mixture having a tightening effect.

According to another particularly advantageous embodiment of the invention, the concentration of polyhydroxylated agent is greater than the concentration of polysaccharide. It was observed that when the concentration of polyhydroxylated agent is greater than the concentration of polysaccharide, a relatively shiny appearance is obtained after application of a composition which contains said mixture having a tightening effect.

According to yet another advantageous feature of this embodiment of the invention, the concentration of poly(vinyl alcohol) (PVA) or of polyvinylpyrrolidone (PVP) is between 3 and 10% by weight with respect to the total weight of said mixture.

According to an advantageous feature, the mixture contains cellulose or one of its derivatives, preferably such as carboxymethylcellulose (CMC), and this at a concentration of between 1 and 8% by weight with respect to the total weight of said mixture.

It was noted that the PVA acts in synergy with the sugar, particularly with the sorbitol, in order to procure a better adhesion to the skin of the cosmetic composition defined further on, and secondly that the PVA in the presence of CMC avoids the sensation of <<pulling>> of the skin, in conferring elasticity to the polymeric matrix which is formed after application of said composition on the skin, without causing in all that a loosening.

The cosmetic composition defined further on, which is prepared from said product, does in fact form a polymer matrix after application on the skin. The creep is defined as the property of the polymer matrix to take shape under the action of a constraint. As for the loosening or the relaxation, it is defined as the property of the polymer matrix to lose the strength of tension when it undergoes a shaping. The term <<plastifying>> refers to qualities of softening and of elasticity of the polymer matrix.

Thus, it was noted that in changing the relative proportions of the four essential constituents of the mixture of the invention, it was possible to vary not only the tightening effect, but also to confer to this mixture an anti-creep action, an anti-loosening action and/or more or less marked plastifying action.

The preferred mixtures according to the invention are constituted of alginate, of sorbitol, of PVA or of PVP and of CMC, in the following proportions:

10 to 80%, preferably 20 to 55%, by weight of alginate, 15 to 75%, preferably 40 to 65%, by weight of sorbitol, 3 to 15%, preferably 3 to 10%, by weight of poly(vinyl alcohol) or polyvinylpyrrolidone, and 0 to 25%, preferably 1 to 8%, by weight of carboxymethylcellulose.

According to a second aspect, the invention relates to the use of the product having a tightening effect as defined above, for the preparation of a cosmetic composition having a tightening effect, with the view to obtaining a mechanical smoothing of the surface of the skin.

An intermediate mixture comprising 5 to 15%, preferably 8 to 10%, of the mixture according to the invention, is in general prepared to this end, in a classical aqueous excipient.

More specifically, the invention relates to novel cosmetic compositions which contain the mixture of the invention.

According to a preferred embodiment of the invention, the mixture of the invention is incorporated in said cosmetic composition at a concentration of 0.2 to 90%, preferably 0.4 to 70%, more preferably 0.4 to 5% and more preferentially 1 to 3%, by weight with respect to the total weight of said composition, of a mixture.

According to a variant of the invention, said composition is characterised in that it further contains at least one biologically active agent such as a moisturising agent, an anti-wrinkle agent, an anti-oxidising agent, an anti-radical agent, an agent which repairs the destructive effects of ultra violet rays or a slimming agent such as caffeine.

According to a preferred embodiment of this variant of the invention, said composition is characterised in that it further contains a perfume, a cosmetically acceptable colouring material and/pr an agent which protects against UVA and UVB ultra violet rays, notably a filter or a nano pigment, such as a zinc oxide or a titanium oxide.

According to various particular embodiments, said cosmetic composition is characterised in that it can be presented in the form of a gel; a lotion, a serum, a suspension, an emulsion, oil-in-water or water-in-oil, or in solid form, e.g. in the form of a stick or a patch, or in dry form, e.g. in the form of a powder.

In order to prepare a dry form in the form of a powder, it will be possible for example to vaporise, in a mixer, the mixture according to the invention, dissolved beforehand in an aqueous excipient, onto a classical cosmetic powder. Of course, the amount of mixture solution vaporised will be compatible with the necessity of the upkeep of the powder form. In general, this amount will not exceed 5%. According to another method of incorporation of the mixture according to the invention in a dry form, it will be possible for it to be fixed onto the excipient, powder, such as talc, e.g. by means of a fluidised air bed.

The composition according to the invention forms a film which has elastomer-type mechanical properties with a texture which lends itself particularly well to make-up, and notably to the use of powders which fix to it particularly well. Moreover, this type of texture possesses anti-migratory properties which can prove to be useful from an aesthetical point of view as well as from the point of view of comfort of use, notably in the proximity of sensitive zones, such as the eyes for example.

According to a third aspect, the present invention relates to another method of cosmetic care, characterised in that it comprises applying topically, on the zones of the skin concerned, an effective amount of a cosmetic composition, as defined above, to obtain a smoothing effect on the surface of the skin.

Advantageously, this method is also characterised in that, further to the application of the cosmetic composition as defined above, and in case of reduction of the tightening effect on the surface of the skin, a moisturisation is carried out of the zones of the skin concerned having received at least one first application of said cosmetic composition, so as to restore said tightening effect, notably by spraying water or a cosmetically acceptable aqueous preparation.

By virtue of the mechanical effect of the tightening effect of the mixture, as defined above, which is incorporated in a cosmetic composition, a partial or total erasure of wrinkles is obtained, and particularly of medium and deep wrinkles. Stated otherwise, a smoothing of the surface of the skin is made which is visible, progressive and durable. Said cosmetic composition also enables numerous imperfections which are present on the surface of the skin to be remedied. Said cosmetic composition does in fact have a non-negligible action upon the reduction of the visibility of certain imperfections which are commonly called <<orange peel>> imperfections, stretch marks, certain scars, as well as certain zones of the skin which usually have folds, such as the neck for example.

The invention has another advantage in comparison with prior art compositions having a tightening effect. As to the difference of these latter compositions, the composition according to the invention has a progressive tightening effect, and this in practice manifests itself by an absence of an effect called <<peak>> effect. The peak effect, for prior art compositions having a tightening effect, leads to a pulling of the skin and even, if necessary, to the rupture and/or to the detachment of the polymer matrix. This peak effect can thus give rise to a brutal and sudden loss of the tightening effect on the surface of the skin.

It will be further noted that the good qualities presented by the composition according to the invention, as to the resistance to creep and to the loosening of the polymer matrix already mentioned, notably enable higher amounts of actives, of fillers or of preservatives for example, to be used.

Furthermore, the mixture according to the invention enables the penetration of the actives to be increased in the skin, and the effect of this is to improve their bioavailability.

Thus, the invention also relates to the use of the mixtures according to the invention as a cosmetic agent for promoting the penetration in the skin of a biologically active agent.

Thus, the mixture according to the invention enables the amount of biologically active agents penetrating in the skin to be increased with respect to a given amount of these agents applied on the surface. The effect of this is to improve their bioavailability, stated otherwise, to increase the amount available of these actives in the lower layers of the skin, and thus to contribute to increasing their effectiveness.

More specifically, the mixture according to the invention, particularly when it has been introduced in the formula of a cosmetic composition containing a biologically active agent, firstly enables an accumulation of said biologically active agent to be obtained in the stratum corneum, commonly called the <<reservoir effect>>, and, secondly, a progressive and prolonged release of this active towards the deepest layers of the skin. In comparison, a cosmetic composition, which would be identical except that it would not contain the mixture according to the invention, would not present this reservoir effect and therefore would not enable the penetration of such a large amount of active in the skin.

Thus, by virtue of the implementation of the present invention, it is notably possible to obtain a double effect: to make a tightening effect of the skin, while at the same time obtaining an improved biological treatment, in particular for biologically reducing or retarding the appearance of wrinkles, for improving or restoring the moisturisation of the skin, for reducing skin pigment marks, or even for obtaining a slimming effect.

Other aims, features and advantages of the invention will appear clearly from the following description which is given from illustrative and non-limiting examples of the invention which represent actually preferred embodiments. In the Examples, all percentages are given by weight, the temperature is ambient temperature, the temperature is given in degrees Celsius and the pressure is atmospheric pressure, unless indicated otherwise.

Figure 2:
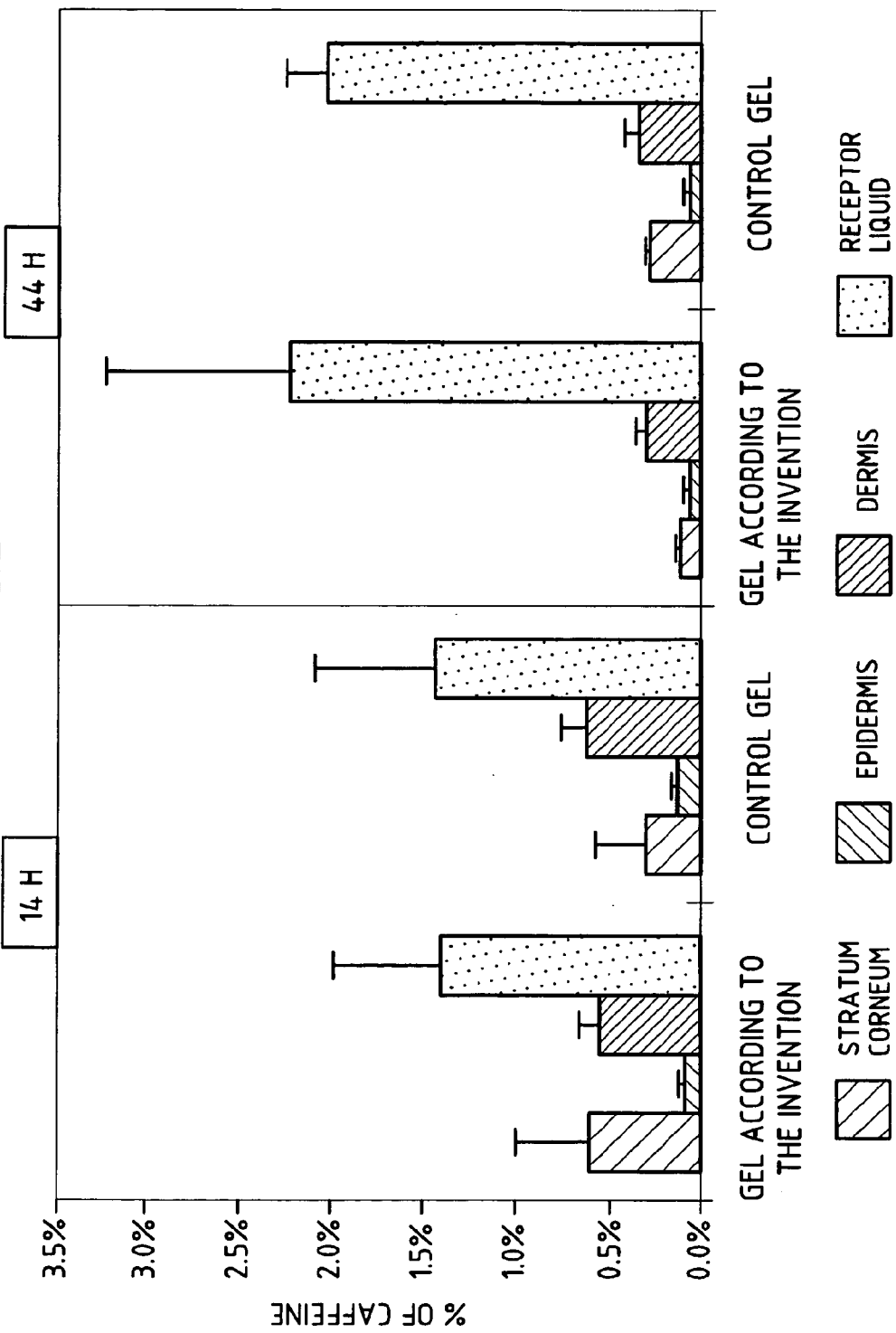

Example 15 is illustrated by FIGS. 1 and 2, which represent, respectively:

FIG. 1: the kinetics of caffeine penetration,

FIG. 2: the distribution of caffeine within skin beds after 14 hours and 44 hours of contact.

EXAMPLE 1

Preparation of an Extract of the Alga *Laminaria flexicaulis*, which is Rich in Alginate in Gel Form 200 g of *Laminaria flexicaulis* alga is used here. Either the entire alga or a part of it, particularly the thalli, can be used.

The algae are first of all rinsed for 1 to 3 hours in cold water in order to remove soluble substances, such as iodides. After having been washed, the algae are dried and then shredded before being bleached. For this, a classical bleaching method is used which consists of using 0.1% bleach and/or 3% hydrogen peroxide. The algae are immersed for a variable duration of 3 to 7 days in baths of bleach and/or baths of hydrogen peroxide. At this stage of preparation, the product is rinsed abundantly with cold water and then finely ground in distilled water with the aid of a Turrax-type turbine at high speed, until a fluid gel is obtained. For this grinding, the proportion of dry product in water is between 1 and 5 liters of water per 200 g of *Laminaria flexicaulis* algae. The extract thus obtained, which is in the form of paste or gel, is colourless or very slightly beige and translucent. It is constituted essentially of alginate and cellulose.

This extract is then advantageously dried according to procedures which are well-known to the person skilled in the art. The dry alga extract thus obtained is ready to be incorporated for the preparation of a product having a tightening effect according to the invention.

EXAMPLE 2

Preparation of an Extract of Sorbs Rich in Sorbitol

Firstly, 50 g of whole sorbs originating from *Sorbus aucuparia* are ground, and 50 ml of distilled water are then added, which is boiled for 10 minutes so as to obtain a reduction of about 60 ml. Filtration is then carried out under pressure (1 to 10 kg/cm$^2$) through a sterile gauze (2 à5 strata, preferably 3) or a glass sieve (100 to 200 μm) inox sinter. A pink coloured juice is thus obtained which can be used as such, or indeed concentrated according to the means of use sought after.

The extract of sorbs thus obtained is ready to be incorporated for the preparation of a product having a tightening effect according to the invention.

Various examples of formulations of products will be given below, which notably have a tightening effect on the surface of the skin, and which constitute a basic product for the preparation of a cosmetic composition according to the invention.

EXAMPLE 3

Mixture According to the Invention having a Very Stiff Tightening Effect

| | |
|---|---|
| Na alginate | 43.00% |
| CMC | 6.75% |
| Concentrate according to Example 2 having 70% of sorbitol | 47.00% |
| PVA | 3% |
| Cellulose | 0.25% |

EXAMPLE 4

Mixture According to the Invention having a Medium Tightening Effect

| | |
|---|---|
| Dry extract of alga according to Example 1 (Extract having 85% of alginate and 5% of cellulose) | 50% |
| Concentrate according to Example 2 having 70% of sorbitol | 46% |
| PVA | 4% |

EXAMPLE 5

Mixture According to the Invention having a Supple Tightening Effect

| | |
|---|---|
| Na alginate | 22% |
| CMC | 4% |
| Concentrate according to Example 2 having 70% of sorbitol | 65% |
| PVA | 9% |

EXAMPLE 6

Mixture According to the Invention having a Tightening Effect Containing PVP

| | |
|---|---|
| Na alginate | 42% |
| CMC | 4% |
| Mannitol | 49% |
| PVP | 5% |

EXAMPLE 7

Mixture having a Tightening Effect According to the Invention

| | |
|---|---|
| Sorbitol | 64.68% |
| Alginate | 22% |
| PVA | 9.15% |
| CMC | 4.17% |

EXAMPLE 8

Tightening Mixture According to the Invention

| | |
|---|---|
| Sorbitol | 40% |
| Sodium alginate | 50% |
| PVA | 6% |
| CMC | 4% |

EXAMPLE 9

Tightening Mixture According to the Invention

| | |
|---|---|
| Sorbitol | 46.05% |
| Sodium alginate | 46.05% |
| PVA | 3.8% |
| CMC | 4.1% |

EXAMPLE 10

Tightening Mixture According to the Invention

| Sorbitol | 47% |
|---|---|
| Alginate | 43% |
| PVA | 3% |
| CMC | 7% |

EXAMPLE 11

Cosmetic Composition Using the Product having a Tightening Effect on the Surface of the Skin According to the Invention Based on Sodium Alginate and Sorbitol

| Mixture according to Example 5 | 8% |
|---|---|
| CMC | 0.33% |
| Phenoxyethanol and paraben | 0.5% |
| Methyl parahydroxybenzoate | 0.1% |
| Purified water | qs 100 |

EXAMPLE 12

Cosmetic Composition According to the Invention in Gel Form

Mixture, having a tightening effect of Example 7 2.8%
Gellified aqueous excipient+preservative+perfume qs 100

EXAMPLE 13

Anti-wrinkles Cosmetic Composition having a Tightening Effect According to the Invention, in Emulsion Form This emulsion is constituted of:

| Mixture, having a tightening effect of Example 7 | 0.8% |
|---|---|
| Extract of tormentilla | 0.5% |
| Fatty phase | 19% |
| Gellified aqueous phase + preservative + perfume | qs 100 |

This composition procures an immediate and prolonged tightening effect, and this enables a smoothing of the skin by a mechanical effect. Moreover, by virtue of the active plant extract for reducing wrinkles, this composition simultaneously, enables an even more durable reducing of wrinkles through a biological effect.

This biological effect is further reinforced by the <<reservoir effect>> which is procured by the presence in the composition of the mixture according to the invention.

EXAMPLE 14

Evaluation of the Immediate Smoothing Effect on Wrinkles, in vivo

1. Method:
An analysis of prints of wrinkles of the skin is made by a method without contact with fringe projections.

This method is commonly used in various industries, notably for measuring the roughness of a surface. This technique is for example described in the publication entitled <<Optical roughness measurements with fringe projections> by Robert Windecker, Stefan Franz, Hans J. Tiziani, Applied optics, 1999, vol. 38, no 13, pp. 2837-2842.

Interference fringes are projected directly onto the skin with the aid of a specific optic and are captured as an image by a digital camera. A phase image is calculated from fringe projection images and the altitude of each point is determined.

Acquisition software enables 2D and 3D measurements of the skin to be obtained and enables the roughness parameters on a profile, the depth and the volume of the wrinkles, to be determined.

2. Protocol:
A zone on a wrinkle at the side of the eye of a volunteer, who had not applied any product on the face since the evening before, is determined and marked off. An image acquisition is then made.

A dose of 2 µL per cm$^2$ of composition according to the invention is applied on this same zone.

A new image of this same zone is then acquired after 45 minutes and 4 hours.

An automatic repositioning enables the specific re-identification of the zone of measurement at each time.

The images are compared with each other and three particular parameters are studied: the mean roughness Ra, the minimum deviation between the highest peak and the deepest valley, Rt, and the mean value of the maxima, Rz.

The mean roughness Ra is defined as the ratio of the surface integrated around the mean value, to the length of skin swept over.

3. Results:
The composition according to Example 13 of the invention applied onto the skin reduces the mean roughness, Ra, of it by 13% after 45 minutes from application and by 21% after 4 hours from application.

The same tests show a lowering of the minimum deviation between the highest peak and the deepest trough, Rt, by 18% after 45 minutes from application and by 14% after 4 hours from application. In the same way, the mean value of the various maxima, Rz, decreases by 14% after 45 minutes from application and by 19% after 4 hours from application.

These results show an immediate smoothing effect on the wrinkles, by virtue of the application of the tightening composition according to the invention.

EXAMPLE 15

Influence of the Mixture According to the Invention Upon the Kinetics of Penetration of Caffeine 1. Aim of the Study
This study is made, in vitro, on human skin, which is kept beforehand by freezing, with the aim of evaluating the influence of the mixture according to the invention on the penetration and the distribution of caffeine within the skin beds. The occlusive properties of a gel according to the invention lead the research of an eventual patch effect. This study is made in comparison with a Carbopol gel.

2. Methodology
The principle of the study is based on the evaluation of the diffusion of an active principle through the thawed human skin which is mounted on Franz cells.

These cells are constituted of two glass elements which delimit an upper partition and a lower partition, and they have an exposed surface area of 3.8 cm. The skin is placed between these two elements, stratum corneum to the top. The active principle deposited on the skin crosses it and is collected in the lower partition, dissolved in a solution which is known as the receptor solution and which is constituted of a phosphate buffer+Na nitride (0.1%) mixture.

The method refers to the COLIPA directives established in the field of in vitro skin absorption moderation (c.f. Validation of the pig ear skin model for in vitro percutaneous absorption: inter-laboratory reproducibility studies. CM. Vincent et al., Perspectives in Percutaneous Penetration, Vol. 7A, 2000).

1 mL of formulation, i.e. 5 mg of active principle (infinite dose), are deposited at random on each explant. The study is made under a non-occlusive condition, so as to promote drying of the polymer and to thus enable an eventual patch effect. The experiments are repeated at the rate of 6 Franz cells per product.

The formulations tested are the following:

| Starting materials in % | Control gel | Gel according to the invention |
|---|---|---|
| Caffeine | 0.5 | 0.5 |
| Stachyose | 1.0 | 1.0 |
| Mixture of Example 7 | — | 1.2 |
| Ethanol | 15.0 | 15.0 |
| Carbopol 940 | 0.5 | 0.5 |
| Triethanolamine | 0.5 | 0.5 |
| Phenoxetol | 0.2 | 0.2 |
| water | 82.3 | 81.1 | a) Penetration Kinetics:

The penetration kinetics are established by samples of the survival liquid between 8 and 40 hours from application.

b) Partitioning:

After 14 hours and 44 hours of contact, half of the cells are demounted and the biopsies undergo a washing treatment during which the excess emulsion on the skin surface is washed with the aid of a <<cotton wool bud>>. The cotton wool buds, as well as the upper part of the cell are immersed in 10 ml of 50/50 methanol/water mixture for 30 minutes with agitation. The solution is then filtered and diluted to a 1/10th in a methanol/water solution (50/50) before determination.

The stratum corneum is collected by 8 successive exfoliations by means of an adhesive strip, by applying a pressure of 300 g/cm$^2$ for 12 seconds. The caffeine is extracted by dissolving in 2 mL of methanol/water under stirring for 30 minutes.

The epidermis is separated from the dermis by heating at 60° C. for 12 seconds, and is then separated from the dermis with the aid of a fine pincer. The caffeine is extracted by contact with 2 ml of methanol/water over 24 hours.

The dermis is placed in 2 mL of methanol/water, for 24 h.

The epidermal and dermal suspensions are agitated for 2 hours and are filtered at 0.45 μm before determination.

The determination of caffeine is made by HPLC.

3. Expression of the Results

The amount of active principle collected within the various biological partitions studied is expressed in μg/mL.

The kinetics of penetration, in μg/cm$^2$ per unit time, is expressed as a function of the interval of confidence, the $IC_{95\%}$, wherein the residual standard deviation is calculated by the ANOVA method over the whole of the tests.

The partitioning is the percentage of caffeine absorbed as a function of time: for each partition studied, the proportion of caffeine absorbed is calculated from the amounts collected with respect to the amounts applied.

4. Results a) Caffeine Solubility Limit:

In order to prevent any risk of under-estimation of the skin absorption, the concentration of active principle in the receptor liquid must be less than 10% of the solubility limit concentration (Guidelines for percutaneous absorption, Colipa, November 95).

At 37° C., the caffeine solubility limit concentration in the receptor liquid is 16 mg/mL. The maximum concentration of caffeine collected during the study is less than 23 μg/mL; the experimental conditions are therefore correct.

b) Caffeine Penetration Kinetics, in vitro:

FIG. 1 indicates the amounts of caffeine collected in the receptor liquid as a function of time.

The kinetics of penetration of caffeine, from the formulation containing the composition according to the invention, is higher than with the control gel based on Carbopol. At 40 hours, the caffeine concentration (33.6 μg/cm$^2$) which is present in the receptor liquid, after application of the gel according to the invention, is greater than that determined after application of the control gel (24.0 μg/cm$^2$).

In drying, the gellifying complex according to the invention causes a slight occlusive effect which promotes the percutaneous absorption of the active principle.

An analysis of variance (ANOVA), which is completed by a Newman-Keuls classification test, was made in order to verify whether a significant difference exists between the amounts absorbed after 12 hours, 40 hours and all times together.

The statistical study made shows that under the experimental conditions, the addition of the mixture according to the invention in a gel significantly promotes the penetration of caffeine in the skin covering.

5. Partition Study:

The proportion of caffeine absorbed is calculated from the amounts collected with respect to the amounts applied.

The distribution of caffeine within the skin beds after 14 and 44 hours of contact is given in the Table below, wherein the results are expressed in %.

| | After 14 hours | | After 44 hours | |
|---|---|---|---|---|
| | Gel of the invention | Control gel | Gel of the invention | Control gel |
| STRATUM CORNEUM | 0.65 | 0.31 | 0.10 | 0.26 |
| EPIDERMIS | 0.10 | 0.11 | 0.04 | 0.04 |
| DERMIS | 0.56 | 0.62 | 0.30 | 0.32 |
| RECEPTOR LIQUID | 1.41 | 1.42 | 2.19 | 2.00 |

The analysis of the results given in the Table above and in FIG. 2 shows a better accumulation of caffeine after 14 hours in the horny layer after application of the gel according to the invention, thus giving an improvement of the reservoir effect of the stratum corneum. This observation is representative of a patch effect.

6. Conclusions

The patch effect of the gel according to the invention manifests itself experimentally by:

A tendency to improve the reservoir effect of the stratum corneum vis-à-vis caffeine, in thus promoting its bioavailability.

Kinetics of caffeine penetration which are significantly higher after addition of the gel according to the invention.

The invention claimed is:

1. A mixture, having a skin-tightening effect, consisting essentially of
   20 to 55% by weight of a polysaccharide having a molecular weight of less than 600,000 Daltons selected from the group consisting of a pectin, a carrageenan, a galactomanane, a xanthan and alginate,
   40 to 75% by weight of a polyhydroxylated agent selected from the group consisting of glucose, sorbitol, mannitol, and galactitol,
   3 to 15% by weight of poly(vinyl alcohol) or polyvinylpyrrolidone, and
   1 to 8% by weight of a cellulose component selected from cellulose carboxymethylcellulose and hydroxymethylcellulose.

2. The mixture according to claim 1, wherein said polysaccharide is an alginate, an alginate of propylene glycol, an alginate in the form of an acid, an alginate in the form of a salt, or a sodium alginate.

3. The mixture according to claim 2, wherein said alginate is in the form of an extract of alga.

4. The mixture of claim 1, wherein said sugar is mannitol.

5. The mixture according to claim 1, wherein said sugar is sorbitol.

6. The mixture according to claim 5, wherein the sorbitol is in the form of a plant extract.

7. The mixture according to claim 1, wherein said hydroxylated agent is at a concentration of between 40 and 65% by weight.

8. The mixture according to claim 1, wherein said mixture contains a *Laminaria flexicaulis* extract and an extract of sorbs.

9. The mixture according to claim 1, wherein the concentration of polysaccharide is greater than the concentration of polyhydroxylated agent.

10. The mixture according to claim 1 wherein the concentration of polyhydroxylated agent is greater than the concentration of polysaccharide.

11. The mixture according to claim 1, wherein said mixture contains 3 to 10% by weight of poly(vinyl alcohol) or polyvinylpyrrolidone.

12. The mixture according to claim 1, consisting essentially of
    20 to 55% by weight of alginate,
    40 to 75% by weight of sorbitol or mannitol,
    3 to 15% by weight of poly(vinyl alcohol) or polyvinylpyrrolidone, and
    1 to 8% by weight of carboxymethylcellulose.

13. A cosmetic composition comprising the mixture of claim 1 in an amount of 0.2 to 90% by weight with respect to the total weight of said cosmetic composition and further comprising at least one cosmetically active agent, selected from a moisturizing agent, an anti-wrinkle agent, an antioxidizing agent, an antiradical agent, an agent which repairs the destructive effects of ultra violet rays, or a slimming agent.

14. The cosmetic composition according to claim 13, wherein said slimming agent comprises caffeine.

15. The cosmetic composition according to claim 13, further comprising at least one selected from a perfume, a cosmetically acceptable colouring material, an agent which protects against UVA or UVB ultra violet rays, a filter or a nano pigment, a zinc oxide or a titanium oxide.

16. The cosmetic composition according, claim 13, wherein said cosmetic composition is in the form of a gel, a lotion, a serum, a suspension, an oil-in-water emulsion, water-in-oil emulsion, in solid form, in stick form, in patch form, in dry form, or in powder form.

17. A method of cosmetic care, comprising applying topically, on the zones of the skin concerned, an effective amount of the cosmetic composition, as defined in claim 13, to obtain a smoothing effect on the surface of the skin.

18. The method according to claim 17, wherein after at least one application of said cosmetic composition on the surface of the skin, a moisturisation is carried out on said surface of the skin, and said surface of the skin is further sprayed with water or a cosmetic aqueous preparation and wherein said tightening effect is restored or increased.

19. The mixture according to claim 1, wherein said polysaccharide has a molecular weight of less than 400,000 Daltons.

20. The mixture according to claim 1, wherein said polysaccharide has a molecular weight of less than 200,000 Daltons.

21. The mixture according to claim 3, wherein said extract of alga is an extract of alga of the family *Laminariacae*.

22. The mixture according to claim 21, wherein said extract of alga of the family *Laminariacae* is selected from *Laminaria digitata* alga, *Laminaria flexicaulis* alga, and *Laminaria saccharina* alga.

23. The mixture according to claim 6, wherein said extract is an extract of sorbs.

24. The mixture according to claim 23, wherein said extract of sorbs is selected from *Sorbus aucuparia* sorb extract, *Sorbus domestica* sorb extract, and *Sorbus aria* sorb extract.

25. The mixture according to claim 8, wherein said extract of sorbs is an extract of *Sorbus aucuparia* sorbs.

26. The mixture according to claim 12, wherein the weight of said sorbitol or mannitol is 40 to 65%.

27. The mixture according to claim 12 wherein the weight of said poly(vinyl alcohol) or polyvinylpyrrolidone is 3 to 10%.

28. The cosmetic composition according to claim 13, wherein said mixture is present in an amount between 0.4 to 70% by weight with respect to the total weight of said cosmetic composition.

29. The cosmetic composition according to claim 13 wherein said mixture is present in an amount between 0.4 to 5% by weight with respect to the total weight of said cosmetic composition.

30. The cosmetic composition according to claim 13, wherein said mixture is present in an amount between 1 to 3% by weight with respect to the total weight of said cosmetic composition.

31. A method of cosmetic care for promoting the penetration in the skin of a biologically active agent, comprising applying topically on the zones of the skin concerned, an effective amount of mixture as defined in claim 1, to obtain said promotion of said penetration of said active agent.

32. A cosmetic composition having a skin-tightening effect, in a form selected from a gel, a lotion, a suspension, an oil-in-water emulsion, a water-in-oil emulsion, a solid form, a stick form, a patch form, a dry form, or a powder form, said composition comprising a mixture consisting essentially of
    20 to 55% by weight of a polysaccharide having a molecular weight of less than 600,000 Daltons selected from the group consisting of a pectin, a carrageenan, a galactomanane, a xanthan and alginate,
    40 to 75% by weight of a polyhydroxylated agent selected from the group consisting of glucose, sorbitol, mannitol, and galactitol,
    3 to 15% by weight of poly(vinyl alcohol) or polyvinylpyrrolidone, and 1 to 8% by weight of a cellulose component selected from cellulose carboxymethylcellulose and hydroxymethylcellulose.

33. The composition according to claim 32, wherein said composition comprises said mixture in an amount ranging between 0.2 and 90% by weight of the total weight of said cosmetic composition.

34. An anti-wrinkle cosmetic composition in emulsion form constituted of:
- 0.8 weight % of a mixture having a tightening effect comprising 64.68 weight % of sorbitol, 22 weight % of alginate, 9.15 weight % of polyvinyl alcohol and 4.17 weight % of carboxymethylcellulose;
- 0.5 weight % of an extract of tormentilla;
- 19 weight % of fatty phase; and
- Qs 100 weight % of a gellified aqueous phase.

* * * * *

UNITED STATES PATENT AND TRADEMARK OFFICE
CERTIFICATE OF CORRECTION

PATENT NO. : 8,986,667 B2
APPLICATION NO. : 12/585755
DATED : March 24, 2015
INVENTOR(S) : Herve Delage-Grouiller, Brigitte Noe and Christian Mahe It is certified that error appears in the above-identified patent and that said Letters Patent is hereby corrected as shown below:

In the Claims

Claim 10, column 13, line 37, "claim 1 wherein" should be changed to --claim 1, wherein--.

Claim 13, column 13, line 56, "or" should be changed to --and--.

Claim 14, column 13, line 59, "wherein said" should be changed to --wherein the at least one cosmetically active agent is a slimming agent and said--.

Claim 16, column 13, line 65, "according, claim 13" should be changed to --according to claim 13--.

Claim 27, column 14, line 34, "claim 12 wherein" should be changed to --claim 12, wherein--.

Claim 29, column 14, lines 41-42, "claim 13 wherein" should be changed to --claim 13, wherein--.

Claim 32, column 14, line 55, "a lotion, a suspension," should be changed to --a lotion, a serum, a suspension,--.

Claim 33, column 15, line 4, cancel the text beginning with "33. The composition" to and ending "cosmetic composition." in column 15, line 7, and insert the following claim:
--33. The cosmetic composition according to claim 32, wherein said cosmetic composition comprises said mixture in an amount ranging between 0.2 and 90% by weight of the total weight of said cosmetic composition.--.

Signed and Sealed this
Seventh Day of July, 2015

Michelle K. Lee
*Director of the United States Patent and Trademark Office*